United States Patent
Laura Lapoint et al.

(10) Patent No.: US 10,500,357 B2
(45) Date of Patent: Dec. 10, 2019

(54) METHODS AND SYSTEMS TO MANAGE CENTRAL SLEEP APNEA BY CONTROLLING ACCUMULATED RETROGRADE VOLUME

(75) Inventors: Manuel Laura Lapoint, Pittsburgh, PA (US); Leonardo Alberto Baloa Welzien, Lake Forest, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 739 days.

(21) Appl. No.: 14/006,544

(22) PCT Filed: Mar. 20, 2012

(86) PCT No.: PCT/IB2012/051325
§ 371 (c)(1),
(2), (4) Date: Sep. 20, 2013

(87) PCT Pub. No.: WO2012/127415
PCT Pub. Date: Sep. 27, 2012

(65) Prior Publication Data
US 2014/0014111 A1    Jan. 16, 2014

Related U.S. Application Data

(60) Provisional application No. 61/467,174, filed on Mar. 24, 2011.

(51) Int. Cl.
*A61M 16/00* (2006.01)
*A61M 16/10* (2006.01)
*A61M 16/16* (2006.01)
*A61M 16/20* (2006.01)

(52) U.S. Cl.
CPC .... *A61M 16/0045* (2013.01); *A61M 16/0051* (2013.01); *A61M 16/024* (2017.08); *A61M 16/161* (2014.02); *A61M 16/202* (2014.02); *A61M 2016/0021* (2013.01); *A61M 2016/0027* (2013.01); *A61M 2016/0039* (2013.01); *A61M 2016/102* (2013.01); *A61M 2202/0225* (2013.01); *A61M 2205/3368* (2013.01);
(Continued)

(58) Field of Classification Search
None
See application file for complete search history.

(56) References Cited

U.S. PATENT DOCUMENTS 3,913,576 A  * 10/1975  Martin .............. A62B 7/02
                                                128/204.25
4,301,810 A  * 11/1981  Belman .............. A61B 5/097
                                                128/200.24
(Continued)

FOREIGN PATENT DOCUMENTS

CA    2708934 A1   5/1998
CN    10188870 A   11/2010
(Continued)

*Primary Examiner* — Tan-Uyen T Ho
*Assistant Examiner* — Jonathan S Paciorek (57) ABSTRACT

Methods and systems to treat Cheyne-Stokes respiration (CSR) and/or central sleep apnea (CSA) include monitoring retrograde breathing and detecting respiratory events. Based on the occurrences of certain respiratory events, a target volume of rebreathing is adjusted to reduce arousals as well as CSR/CSA.

17 Claims, 3 Drawing Sheets

(52) U.S. Cl.
CPC ... *A61M 2205/502* (2013.01); *A61M 2205/52* (2013.01); *A61M 2230/60* (2013.01)

(56) References Cited

U.S. PATENT DOCUMENTS

| | | | | |
|---|---|---|---|---|
| 5,623,923 | A * | 4/1997 | Bertheau | A62B 18/084 128/201.22 |
| 6,622,725 | B1 * | 9/2003 | Fisher | A61M 16/08 128/203.12 |
| 6,752,150 | B1 * | 6/2004 | Remmers | A61M 16/0009 128/204.18 |
| 7,073,501 | B2 | 7/2006 | Remmers et al. | |
| 2003/0154979 | A1 * | 8/2003 | Berthon-Jones | A61M 16/00 128/204.18 |
| 2004/0216740 | A1 * | 11/2004 | Remmers | A61M 16/00 128/204.18 |
| 2005/0039745 | A1 * | 2/2005 | Stahmann | A61N 1/362 128/204.18 |
| 2007/0221224 | A1 * | 9/2007 | Pittman | A61M 16/0069 128/204.22 |
| 2008/0302364 | A1 * | 12/2008 | Garde | A61M 16/0045 128/204.23 |
| 2009/0133696 | A1 * | 5/2009 | Remmers | A61M 16/0488 128/204.26 |
| 2011/0297156 | A1 * | 12/2011 | Shelly | A61M 16/00 128/204.23 |

FOREIGN PATENT DOCUMENTS

| | | | |
|---|---|---|---|
| WO | 200045882 | A1 | 8/2000 |
| WO | 2009012599 | A1 | 1/2009 |

* cited by examiner

METHODS AND SYSTEMS TO MANAGE CENTRAL SLEEP APNEA BY CONTROLLING ACCUMULATED RETROGRADE VOLUME

The present disclosure pertains to methods and systems for treating central sleep apnea for patients (or "subjects").

One commercialized technology to treat subjects having Cheyne-Stokes Respiration (CSR) is servo ventilation. Servo ventilation devices (or airway pressure devices) provide respiratory support to (temporarily) compensate for the lack of subject effort (or reduced level of subject effort) to breathe. The usage of servo ventilation could cause arousals and hyperventilation.

It is an object of one or more embodiments of the present disclosure to provide a system for treating central sleep apnea of a subject using accumulated retrograde volume of breathable gas at or near the airway of a subject. The system includes one or more sensors that generate output signals related to parameters of the breathable gas at or near the airway of the subject; a respiratory event module configured to detect occurrences of respiratory events based on the generated output signals; and a rebreathing module configured to adjust a rebreathing level of the subject based on detected occurrences of respiratory events.

It is yet another aspect of one or more embodiments of the present disclosure to provide a method of treating central sleep apnea of a subject having an airway, using accumulated retrograde volume of breathable gas at or near the airway of the subject. The method includes generating output signals conveying information related to parameters associated with breathable gas at or near the airway of the subject; detecting occurrences of respiratory events based on the generated output signals; and adjusting a rebreathing level of the subject based on the detected occurrences.

It is yet another aspect of one or more embodiments to provide a system configured to treat central sleep apnea of a subject having an airway, using accumulated retrograde volume of breathable gas at or near the airway of the subject. The system includes a means for generating one or more signals conveying information related to one or more parameters associated with breathable gas at or near the airway of the subject; a means for detecting occurrences of respiratory events based on the one or more generated output signals; and a means for adjusting a rebreathing level of the subject based on the detected occurrences.

These and other objects, features, and characteristics of the various embodiments, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
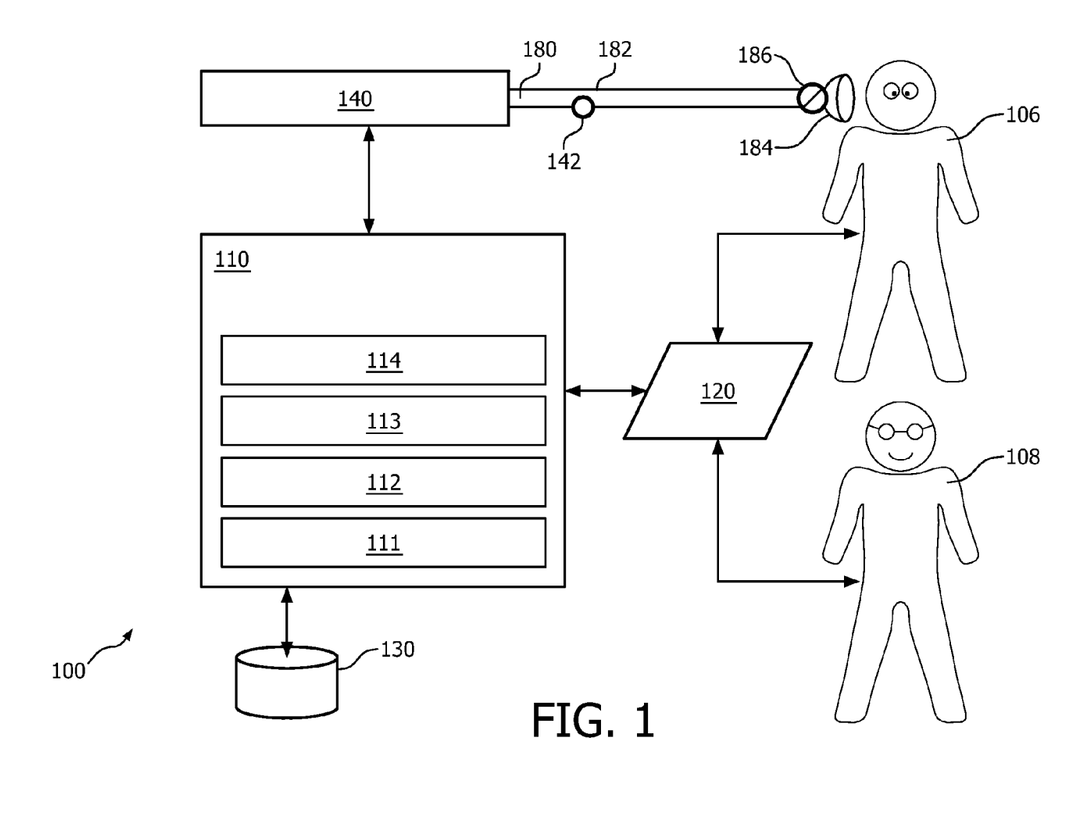
FIG. 1 schematically illustrates a system configured to treat central sleep apnea of a subject.

FIG. 1 schematically illustrates a system 100 configured to treat central sleep apnea of a subject. In particular, system 100 monitors the breathing of a subject 106, as characterized by breathing parameters, to detect occurrences of respiratory events including Cheyne-Stokes respiration, hyperventilation, and/or other respiratory events. Based on these occurrences, breathing parameters, and/or other information, system 100 monitors accumulated retrograde breathing and non-intrusively adjusts the volume of exhaled rebreathing and/or other system settings affecting the subject's breathing. Through these non-intrusive adjustments, system 100 aims to prevent or reduce arousals, hyperventilation, apneas, and/or other respiratory events. In one embodiment, system 100 comprises one or more of a processor 110, a pressure generator 140, a sensor 142, an electronic storage 130, a user interface 120, a subject interface 180, and/or other components.

Pressure generator 140 may be integrated, combined, coupled, or connected with a (positive) airway pressure device. Pressure generator 140 is configured to provide a pressurized flow of breathable gas to the airway of subject 106, e.g. via subject interface 180. Subject 106 may or may not initiate respiration. In certain embodiments, pressure support is implemented as a higher and lower positive pressure of a (multi-level) PAP device, respectively. For example, to support inspiration, the pressure of the pressurized flow of breathable gas is increased to an Inspiratory Positive Air Pressure (IPAP). Similarly, to support expiration, the pressure of the pressurized flow of breathable gas is decreased to an Expiratory Positive Air Pressure (EPAP). Other schemes for providing respiratory support (including BiPAP) through the delivery of the pressurized flow of breathable gas are contemplated.

An airway pressure device may be configured such that one or more gas parameters of the pressurized flow of breathable gas are controlled in accordance with a therapeutic respiratory regimen for subject 106. The one or more gas parameters include one or more of flow, volume, retrograde volume, accumulated retrograde volume, pressure, humidity, velocity, acceleration, (intentional) gas leak, and/or other parameters. In certain embodiments system 100 is configured to provide types of therapy other than ventilation, including types of therapy where a subject performs inspiration and/or expiration of his own accord or where the device provides negative pressure.

In certain embodiments, pressure generator 140 may be integrated, combined, coupled, or connected with a (servo) ventilator or an adaptive servo ventilator (ASV). As before, system 100 monitors breathing, rebreathing, and/or occurrences of respiratory events and adjusts the volume of exhaled rebreathing and/or other system settings affecting the subject's breathing.

A pressurized flow of breathable gas is delivered from pressure generator 140 to or near the airway of subject 106 by a subject interface 180. Subject interface 180 includes a conduit 182, a subject interface appliance 184, and/or other components. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140. Subject interface 180 includes a rebreathing system 186 configured to control the rebreathing level of subject 106. In certain embodiments, rebreathing system 186 includes a breathing mask having a controllable exhalation port. Rebreathing system 186 is configured to control the rebreathing level by adjusting the amount and/or volume of intentional leak of system 100 or its constituent components, e.g. through controllable valves. Rebreathing system 186 may be located on subject interface appliance 184, conduit 182, at the junction between appliance 184 and conduit 182, and/or at other locations.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. In certain embodiments, subject interface appliance 184 is combined, coupled, integrated, and/or connected to rebreathing system 186 and/or any of its constituent components. The present disclosure is not limited to these examples, and contemplates delivery of the pressurized flow of breathable gas to subject 106 using any subject interface.

System 100 may include electronic storage 130 comprising electronic storage media that electronically stores information. The electronic storage media of electronic storage 130 includes one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 stores software algorithms, information determined by processor 110, information received via user interface 120, and/or other information that enables system 100 to function properly. For example, electronic storage 130 records or stores one or more (breathing) parameters and/or other parameters (as discussed elsewhere herein), information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, and/or other information. Electronic storage 130 may be a separate component within system 100, or electronic storage 130 may be provided integrally with one or more other components of system 100 (e.g., processor 110).

System 100 may include user interface 120 configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 controls the radiation source to emit light in a manner that conveys to subject 106 information related to breathing and/or the pressurized flow of breathable gas. Note that the subject and the user of system 100 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 is configured to generate one or more output signals conveying measurements related to respiratory parameters, including one or more of flow, pressure, humidity, velocity, acceleration, and/or other respiratory parameters. Output signals may convey measurements related to parameters of thoracic respiratory effort, abdominal respiratory effort, and/or other respiratory effort parameters. Based on these respiratory parameter and/or respiratory effort parameters, parameter determination module 111 (and/or other components of system 100) may be configured to determine one or more breathing parameters, including (tidal) volume, retrograde volume, accumulated retrograde volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Sensor 142 may be in fluid communication with conduit 182 and/or subject interface appliance 184.

The illustration of sensor 142 as including a single member in FIG. 1 is not intended to be limiting. In certain embodiments sensor 142 includes a plurality of sensors operating as described above by generating output signals conveying information related to parameters associated with the gas breathed or rebreathed by subject 106, the delivery of the gas to subject 106, and/or a respiratory effort by the subject. For example, a breathing parameter may be related to a mechanical unit of measurement of a component of system 100 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of system 100. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a parameter determination module 111, a control module 112, a respiratory event module 113, a rebreathing module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

In certain embodiments, system 100 includes a parameter determination module 111 configured to determine one or more breathing parameters from the output signals generated by sensor(s) 142. The one or more breathing parameters may include a respiratory parameter derived from one or more gas parameters of the pressurized flow of breathable gas. Such parameters include one or more of a tidal volume of the breathing of the subject, a retrograde volume, a respiratory rate, an inhalation time, an exhalation time, a flow rate of the breathing of the subject, and/or other breathing parameters. Such breathing parameters may be related to and/or derived from measurements of one or more of (peak) flow, pressure, temperature, humidity, velocity, acceleration, gas composition (e.g. concentration(s) of one or more constituents), thermal energy dissipated, (intentional) gas leak, and/or other gas parameters related to the (pressurized) flow of breathable gas. The breathing parameters may indicate a respiratory effort of subject 106. This includes one or more of a thoracic respiratory effort, an abdominal respiratory effort of the subject, and/or other parameters indicating respiratory effort. Some or all of the stated functionality of parameter determination module 111 may be incorporated or integrated into other computer program modules of processor 110.

In certain embodiments, system 100 includes a control module 112 configured to control pressure generator 140 in the provision of adjusting pressure levels for system 100. As such, control module 112 controls aspects or settings affecting the breathing and rebreathing of the subject, e.g. in accordance with a therapy regime, with the objective to adjust one or more parameters of the respiration of subject 106. Such respiratory parameters include parameters determined by parameter determination module 111 and/or other respiratory parameters. A determined parameter may be used by control module 112 in a feedback manner to adjust system settings. For example, responsive to a change in the rate of breathing, the tidal volume of subject 106 may change.

Respiratory event module 113 is configured to detect an occurrence of a respiratory event, e.g. based on output signals generated by sensor 142 and/or parameters determined by parameter determination module 111. For example, respiratory event module 113 can detect occurrences of Cheyne-Stokes respiration, central sleep apneas, obstructive sleep apneas, hypopneas, snoring, hyperventilation, lack (or significantly reduced level) of respiratory effort (e.g., thoracic respiratory effort and/or abdominal respiratory effort), and/or other respiratory events. Note that a lack of effort may be accompanied by a significant reduction in tidal volume (and/or changes in other breathing/rebreathing parameters).

Figure 2A:
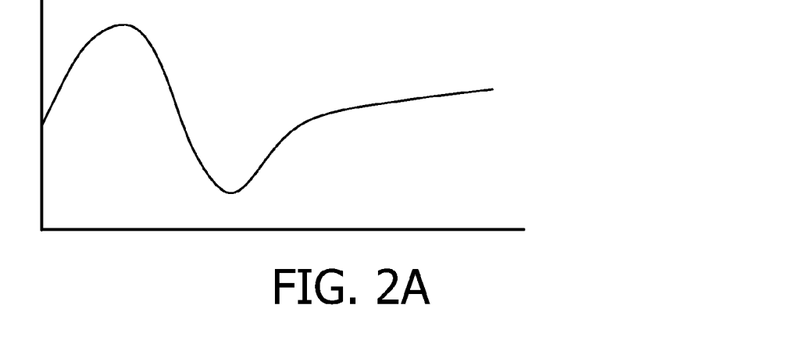
FIGS. 2A, 2B, and 2C illustrate flow diagrams that exemplify the operation of certain embodiments disclosed herein.
Figure 2B:
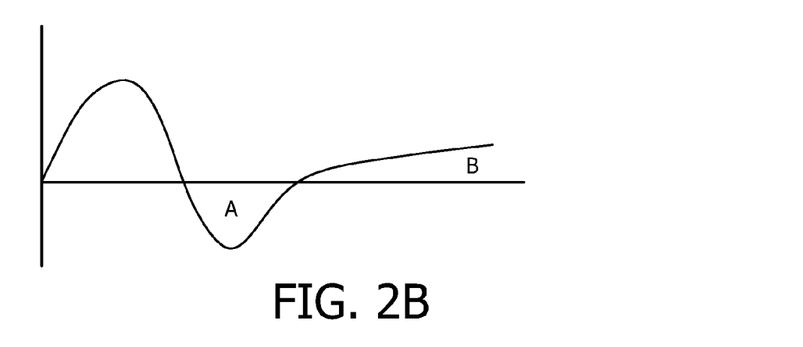

Rebreathing module 114 is configured to adjust a rebreathing level of the subject based on detected occurrences of respiratory events. By rebreathing exhaled air (or other breathable gas) a subject may prevent central sleep apneas (or CSR). The rebreathing level, or volume of rebreathed air, is also referred to as the retrograde volume. To adjust the retrograde volume, rebreathing module 114 controls rebreathing system 186. For example, rebreathing module may include a controllable exhalation port carried by subject interface appliance 184. System 100 can control the accumulated retrograde volume of a subject by controlling the amount or level of intentional leak, e.g. through the exhalation port. For example, system 100 may be able to open or close the exhalation port. By way of illustration, FIG. 2A illustrates a flow diagram (flow on Y-axis, e.g. in liters, and time on the X-axis) for a subject using PAP support in conjunction with a mask having its exhalation port open. FIG. 2B illustrates a similar diagram, but this time with the exhalation port closed. This forces the subject to rebreathe exhaled air. The difference between areas "A" and "B" in FIG. 2B represents the retrograde volume for one full breath.

Retrograde volume "$V_R$" may be calculated according to the following formula:

$$V_R = \int F_A dt + \int F_S dt,$$

wherein "F" represents the flow on the Y-axis in FIG. 2B. Note that exhaled air is richer in $CO_2$ than atmospheric air. If the exhalation port remains closed, the accumulated retrograde volume (e.g. in or near subject interface appliance 184 and/or conduit 182) increases. As a result, system 100 is capable of providing more $CO_2$ to the subject. Accumulated retrograde volume may be calculated according to the following formula:

$$V_{A,R} = \sum_{i=0}^{N} V_{Ri},$$

wherein "N" represents an adjustable number of breaths, and "i" represents the number of breaths for which the exhalation port is closed. Other methods of adjusting the rebreathing level, e.g. through intentional leak, are also contemplated.

Figure 2C:
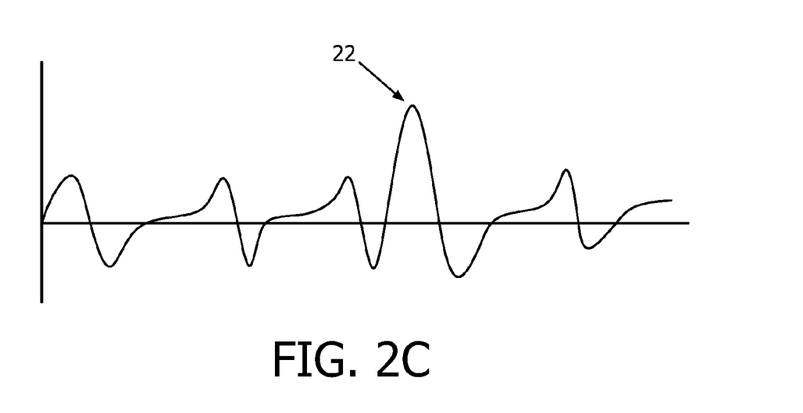

FIGS. 2A, 2B, and 2C illustrate flow diagrams that exemplify the operation of certain embodiments disclosed herein. FIG. 2C illustrates a flow diagram of multiple full breaths for a case in which the rebreathing level is set too high, e.g. 800 ml. This rebreathing level corresponds to system 100 closing the exhalation port too long, and thus causing a subject to experience hyperventilation. The occurrence of hyperventilation is indicated by item 22 in FIG. 2C. On the other hand, if the rebreathing level is set too low, e.g. 400 ml, the subject may still experience Cheyne-Stokes respirations. Rebreathing module 114 thus adjusts the rebreathing level (e.g. through controlling the exhalation port of a breathing mask) based on the occurrence of respiratory events to a level fitting for a particular subject, and optionally adjusted throughout the use by that particular subject of system 100. Rebreathing levels (and/or nightly patterns of rebreathing levels) for multiple subjects may be stored in electronic storage 130 for future use and/or analysis.

Figure 3:
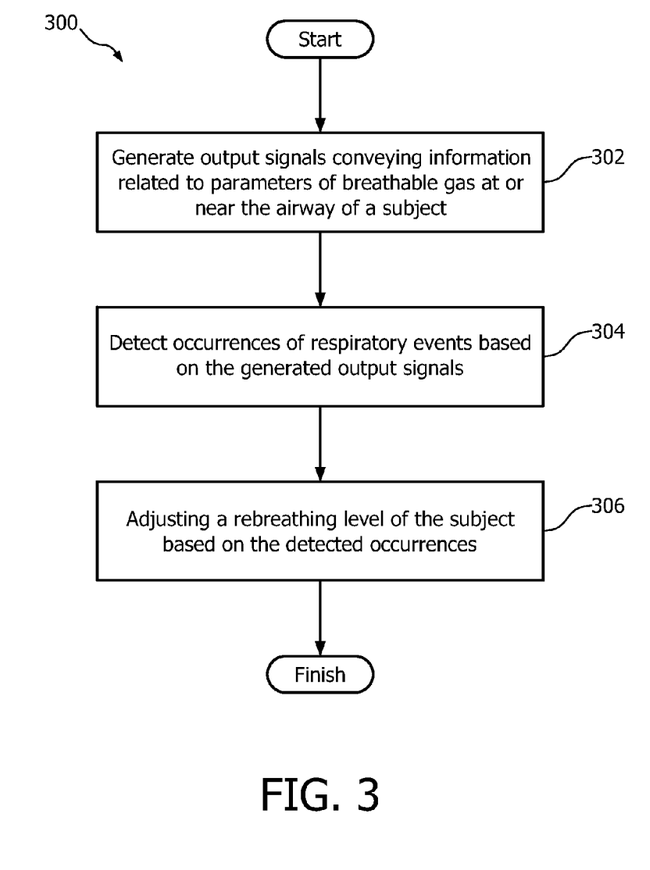
FIG. 3 illustrates a method for treating central sleep apnea of a subject.

FIG. 3 illustrates a method 300 for treating central sleep apnea of a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, output signals are generated conveying information related to parameters of breathable gas at or near the airway of a subject. In one embodiment, operation 302 is performed by a sensor similar to or substantially the same as sensor 142 (shown in FIG. 1 and described above).

At an operation 304, occurrences of respiratory events are detected based on the generated output signals. In one embodiment, operation 304 is performed by a respiratory event module similar to or substantially the same as respiratory event module 113 (shown in FIG. 1 and described above).

At an operation 306, a rebreathing level of the subject is adjusted based on the detected occurrences of respiratory events. This may include determining a new rebreathing level based on the detected occurrences of respiratory events, and/or implementing the new rebreathing level. In one embodiment, operation 306 is performed by a rebreathing module similar to or substantially the same as rebreathing module 114 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the operation of embodiments has been described in detail for the purpose of illustration based on what is currently considered to be the most practical and preferred implementations, it is to be understood that such detail is solely for that purpose and that the disclosed embodiments are not to be interpreted as limiting, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system for treating central sleep apnea of a subject having an airway, using accumulated retrograde volume of breathable gas at or near the airway of the subject, the system comprising:
   a subject interface, the subject interface comprises a rebreathing system configured to control rebreathing of the subject, wherein the rebreathing system comprises a controllable exhalation port;
   one or more sensors that generate one or more output signals conveying measurements related to one or more parameters of the breathable gas at or near the airway of the subject; and
   one or more processors configured to execute computer program modules, the computer program modules comprising:
   a parameter determination module configured to determine one or more breathing parameters from the output signals, wherein the parameter determination module is configured to determine an accumulated retrograde volume of breathable gas at or near the airway of the subject wherein the retrograde volume is a volume of rebreathed exhaled breathable gas, and wherein determining the accumulated retrograde volume of breathable gas at or near the airway of the subject comprises a summation of the retrograde volume over two or more breaths during which the exhalation port is closed;

a respiratory event module configured to detect occurrences of respiratory events
based on the breathing parameters, the respiratory events comprising: Cheyne-Stokes respiration, central sleep apneas, obstructive sleep apneas, hypopneas, snoring, hyperventilation, and/or lack of respiratory effort, and wherein the respiratory events include a first type of respiratory event and a second type of respiratory event, wherein the first type of respiratory event is different from the second type of respiratory event; and a rebreathing module configured to adjust the accumulated retrograde volume of breathable gas of the subject based on detected occurrences of respiratory events by the respiratory event module, wherein the rebreathing module is configured to increase the accumulated retrograde volume of breathable gas of the subject based on one or more detected occurrences of the first type of respiratory event, and wherein the rebreathing module is further configured to decrease the accumulated retrograde volume of breathable gas of the subject based on one or more detected occurrences of the second type of respiratory event.

2. The system of claim 1, wherein the rebreathing module is configured to increase the accumulated retrograde volume of breathable gas of the subject responsive to a detected occurrence of the first type of respiratory event, and wherein the rebreathing module is further configured to decrease the accumulated retrograde volume of breathable gas of the subject responsive to a detected occurrence of the second type of respiratory event.

3. The system of claim 1, wherein the first type of respiratory event includes Cheyne-Stokes respiration.

4. The system of claim 1, wherein the second type of respiratory event includes hyperventilation.

5. The system of claim 1, wherein the rebreathing module is configured to adjust the accumulated retrograde volume of breathable gas of the subject by one or both of
regulating the exhalation port of the patient interface used to deliver breathable gas at or near the airway of the subject, and/or
regulating an amount of intentional leak associated with the breathable gas at or near the airway of the subject.

6. The system of claim 1, wherein the first type of respiratory event includes one or more of a central sleep apnea, an obstructive sleep apnea, and/or a hypopnea.

7. The system of claim 1, wherein detection of occurrences of the second type of respiratory event is based on one or both of thoracic respiratory effort and/or abdominal respiratory effort.

8. A method of treating central sleep apnea of a subject having an airway, using accumulated retrograde volume of breathable gas at or near the airway of the subject, with a system comprising a subject interface including a controllable exhalation port, and one or more sensors, the method comprising:
generating, with the one or more sensors, one or more output signals conveying measurements related to one or more parameters associated with breathable gas at or near the airway of the subject;
determining one or more breathing parameters from the output signals, wherein determining the one or more parameters includes determining an accumulated retrograde volume of breathable gas at or near the airway of the subject over, wherein the retrograde volume is a volume of rebreathed exhaled breathable gas, and wherein determining the accumulated retrograde volume of breathable gas at or near the airway of the subject comprises summation of retrograde volume over two or more breaths during which the exhalation port is closed;
detecting occurrences of respiratory events based on the one or more breathing parameters, wherein the respiratory events include a first type of respiratory event and a second type of respiratory event, the respiratory events comprising: Cheyne-Stokes respiration, central sleep apneas, obstructive sleep apneas, hypopneas, snoring, hyperventilation, and/or lack of respiratory effort, and wherein the first type of respiratory event is different from the second type of respiratory event; and
adjusting the accumulated retrograde volume of breathable gas of the subject based on the detected occurrences, wherein the accumulated retrograde volume of breathable gas of the subject is increased based on one or more detected occurrences of the first type of respiratory event, and wherein the accumulated retrograde volume of breathable gas level of the subject is decreased based on one or more detected occurrences of the second type of respiratory event.

9. The method of claim 8, wherein adjusting the accumulated retrograde volume of breathable gas includes increasing the accumulated retrograde volume of breathable gas of the subject responsive to a detected occurrence of the first type of respiratory event, and wherein adjusting the accumulated retrograde volume of breathable gas includes decreasing the accumulated retrograde volume of breathable gas of the subject responsive to a detected occurrence of the second type of respiratory event.

10. The method of claim 8, wherein the first type of respiratory event includes Cheyne-Stokes respiration.

11. The method of claim 8, wherein the second type of respiratory event includes hyperventilation.

12. The method of claim 8, wherein adjusting the accumulated retrograde volume of breathable gas includes one or both of
regulating the exhalation port of the patient interface used to deliver breathable gas at or near the airway of the subject, and/or
regulating an amount of intentional leak associated with the breathable gas at or near the airway of the subject.

13. A system configured to treat central sleep apnea of a subject having an airway, using accumulated retrograde volume of breathable gas at or near the airway of the subject, the system comprising:
a subject interface means, the subject interface means comprises a rebreathing means configured to control rebreathing of the subject, wherein the rebreathing means comprises a controllable exhalation port;
means for generating one or more signals conveying measurements related to one or more parameters associated with breathable gas at or near the airway of the subject;
means for determining one or more breathing parameters from the output signals, wherein the means for determining is configured to determine an accumulated retrograde volume of breathable gas at or near the airway of the subject over, wherein the retrograde volume is a volume of rebreathed exhaled breathable gas, and wherein determining the accumulated retrograde volume of breathable gas at or near the airway of the subject comprises summation of retrograde volume over two or more breaths during which the exhalation port is closed;

means for detecting occurrences of respiratory events based on the one or more generated output signals, the respiratory events comprising: Cheyne-Stokes respiration, central sleep apneas, obstructive sleep apneas, hypopneas, snoring, hyperventilation, and/or lack of respiratory effort, and wherein the respiratory events include a first type of respiratory event and a second type of respiratory event, wherein the first type of respiratory event is different from the second type of respiratory event; and means for adjusting accumulated retrograde volume of breathable gas of the subject based on the detected occurrences, wherein accumulated retrograde volume of breathable gas of the subject is increased based on one or more detected occurrences of the first type of respiratory event, and wherein the accumulated retrograde volume of breathable gas of the subject is decreased based on one or more detected occurrences of the second type of respiratory event.

14. The system of claim 13, wherein the means for adjusting the accumulated retrograde volume of breathable gas is configured to increase the accumulated retrograde volume of breathable gas of the subject responsive to a detected occurrence of the first type of respiratory event, and wherein the means for adjusting the accumulated retrograde volume of breathable gas is further configured to decrease the accumulated retrograde volume of breathable gas of the subject responsive to a detected occurrence of the second type of respiratory event.

15. The system of claim 13, wherein the first type of respiratory event includes Cheyne-Stokes respiration.

16. The system of claim 13, wherein the second type of respiratory event includes hyperventilation.

17. The system of claim 13, wherein the means for adjusting the accumulated retrograde volume of breathable gas of the subject includes:

means for regulating the exhalation port of the subject interface used to deliver breathable gas at or near the airway of the subject and/or for regulating an amount of intentional leak associated with the breathable gas at or near the airway of the subject.

* * * * *